US005636779A

United States Patent [19]
Palmer

[11] Patent Number: 5,636,779
[45] Date of Patent: Jun. 10, 1997

[54] APPARATUS FOR APPLYING SURGICAL FASTENERS

[75] Inventor: Mitchell J. Palmer, New Milford, Conn.

[73] Assignee: United States Surgical Corporation, Norwalk, Conn.

[21] Appl. No.: 355,126

[22] Filed: Dec. 13, 1994

[51] Int. Cl.⁶ .................................................. A61B 17/068
[52] U.S. Cl. .................... 227/175.2; 227/176.1; 227/180.1; 227/182.1; 227/19
[58] Field of Search .................... 227/19, 175.1, 227/175.2, 175.3, 175.4, 176.1, 180.1, 182.1, 8

[56] References Cited

U.S. PATENT DOCUMENTS

| | | |
|---|---|---|
| D. 283,733 | 5/1986 | Rawson et al. . |
| D. 322,143 | 12/1991 | Spreckelmeier . |
| 2,174,219 | 9/1939 | Balma . |
| 2,246,647 | 6/1941 | Vancura . |
| 3,079,606 | 3/1963 | Bobrov et al. . |
| 3,490,675 | 1/1970 | Green et al. . |
| 3,494,533 | 2/1970 | Green et al. . |
| 3,499,591 | 3/1970 | Green . |
| 3,675,688 | 7/1972 | Bryan et al. . |
| 3,692,224 | 9/1972 | Astafiev et al. . |
| 3,735,762 | 5/1973 | Bryan et al. . |
| 3,795,034 | 3/1974 | Strekopytov et al. . |
| 3,844,289 | 10/1974 | Noiles . |
| 3,873,016 | 3/1975 | Fishbein . |
| 4,006,786 | 2/1977 | Speicher . |
| 4,086,926 | 5/1978 | Green et al. . |
| 4,108,306 | 8/1978 | Samuels et al. . |
| 4,202,479 | 5/1980 | Razgulov et al. . |
| 4,202,480 | 5/1980 | Annett . |
| 4,256,251 | 3/1981 | Moshofsky . |
| 4,296,881 | 10/1981 | Lee . |
| 4,304,236 | 12/1981 | Conta et al. . |
| 4,305,539 | 12/1981 | Korolkov et al. . |
| 4,319,576 | 3/1982 | Rothfuss . |
| 4,331,276 | 5/1982 | Bourque . |
| 4,349,028 | 9/1982 | Green . |
| 4,354,628 | 10/1982 | Green . |

(List continued on next page.)

FOREIGN PATENT DOCUMENTS

| | | |
|---|---|---|
| 5476486 | 9/1986 | Australia . |
| 5476586 | 9/1986 | Australia . |
| 0324638 | 7/1989 | European Pat. Off. . |
| 0373762 | 6/1990 | European Pat. Off. . |
| 0380025 | 8/1990 | European Pat. Off. . |
| 0489436 | 6/1992 | European Pat. Off. . |
| 0596543 | 5/1994 | European Pat. Off. . |
| 2070499 | 9/1981 | United Kingdom . |
| 8302247 | 7/1983 | WIPO . |
| WO9523557 | 9/1995 | WIPO . |

OTHER PUBLICATIONS

Flickinger et al. Surgical Stapling Gastric and Small Bowel Procedures pp. 1–145, 1988.
Anderson et al. Surgical Stapling Thoraci, Vascular and Esophageal Procedures pp. 1–101, 1988.
Brolin et al. Surgical Stapling Bariatric Procedures for Morbid Obesity pp. 1–115, 1989.
"Auto Suture® Premium Poly CS™–57 Disposable Surgical Stapler," printed 1986, reprinted 1990.
"Auto Suture® Poly CS™–57 Disposable Surgical Stapler", printed Jul. 1988.
"Auto Suture® Poly CS™–57 Disposable Loading Units with LACTOMER Absorbable Copolymer Staples", printed Jul. 1988.
U.S. application No. Re. 90/002229, Fox et al., Aug. 1981.

Primary Examiner—Scott A. Smith

[57] ABSTRACT

A surgical fastener applying apparatus having elongated cartridge and anvil half sections which are relatively moveable from an unclamped to a clamped position. A safety member is supported in the cartridge support member and movable between a non-blocking position and a blocking position to prevent relative movement of the cartridge and anvil half sections to the clamped position after the fasteners have been fired. The safety member blocks movement of the clamping lever to the clamping position.

19 Claims, 10 Drawing Sheets

U.S. PATENT DOCUMENTS

| | | |
|---|---|---|
| 4,383,634 | 5/1983 | Green . |
| 4,391,401 | 7/1983 | Moshofsky . |
| 4,415,112 | 11/1983 | Green . |
| 4,429,695 | 2/1984 | Green . |
| 4,442,964 | 4/1984 | Becht . |
| 4,473,077 | 9/1984 | Noiles et al. . |
| 4,480,640 | 11/1984 | Becht . |
| 4,500,025 | 2/1985 | Skwor . |
| 4,506,670 | 3/1985 | Crossley . |
| 4,508,253 | 4/1985 | Green . |
| 4,519,532 | 5/1985 | Foslien . |
| 4,520,817 | 6/1985 | Green . |
| 4,523,695 | 6/1985 | Braun et al. . |
| 4,527,724 | 7/1985 | Chow et al. . |
| 4,530,453 | 7/1985 | Green . |
| 4,540,110 | 9/1985 | Bent et al. . |
| 4,556,058 | 12/1985 | Green . |
| 4,568,009 | 2/1986 | Green . |
| 4,569,346 | 2/1986 | Poirier . |
| 4,576,165 | 3/1986 | Green et al. . |
| 4,576,167 | 3/1986 | Noiles . |
| 4,589,582 | 5/1986 | Bilotti . |
| 4,591,085 | 5/1986 | Di Giovanni . |
| 4,592,498 | 6/1986 | Braun et al. . |
| 4,597,517 | 7/1986 | Wagdy . |
| 4,605,004 | 8/1986 | Di Giovanni et al. . |
| 4,606,344 | 8/1986 | Di Giovanni . |
| 4,606,345 | 8/1986 | Dorband et al. . |
| 4,607,636 | 8/1986 | Kula et al. . |
| 4,608,981 | 9/1986 | Rothfuss et al. . |
| 4,612,933 | 9/1986 | Brinkerhoff et al. . |
| 4,617,928 | 10/1986 | Alfranca . |
| 4,633,861 | 1/1987 | Chow et al. . |
| 4,633,874 | 1/1987 | Chow et al. . |
| 4,646,745 | 3/1987 | Noiles . |
| 4,664,305 | 5/1987 | Blake, III et al. . |
| 4,665,916 | 5/1987 | Green . |
| 4,684,051 | 8/1987 | Akopov et al. . |
| 4,714,187 | 12/1987 | Green . |
| 4,715,520 | 12/1987 | Roehr, Jr. et al. . |
| 4,728,020 | 3/1988 | Green et al. . |
| 4,741,336 | 5/1988 | Failla et al. . |
| 4,807,628 | 2/1989 | Peters et al. . |
| 4,809,898 | 3/1989 | Gassner et al. . |
| 4,850,355 | 7/1989 | Brooks et al. . |
| 4,863,088 | 9/1989 | Redmond et al. . |
| 4,869,415 | 9/1989 | Fox . |
| 4,881,544 | 11/1989 | Green . |
| 4,881,545 | 11/1989 | Isaacs et al. . |
| 4,892,244 | 1/1990 | Fox et al. . |
| 4,915,100 | 4/1990 | Green . |
| 4,938,408 | 7/1990 | Bedi et al. . |
| 4,941,623 | 7/1990 | Pruitt . |
| 4,955,959 | 9/1990 | Tompkins et al. . |
| 5,031,814 | 7/1991 | Tompkins et al. . |
| 5,040,715 | 8/1991 | Green et al. . |
| 5,065,929 | 11/1991 | Schulze et al. . |
| 5,071,052 | 12/1991 | Rodak et al. . |
| 5,074,454 | 12/1991 | Peters . |
| 5,083,695 | 1/1992 | Foslien et al. . |
| 5,100,042 | 3/1992 | Gravener et al. . |
| 5,106,008 | 4/1992 | Tompkins et al. . |
| 5,129,570 | 7/1992 | Schulze et al. . |
| 5,395,034 | 3/1995 | Allen et al. .................... 227/19 |
| 5,413,267 | 5/1995 | Solyntjes et al. .............. 227/175.4 |
| 5,447,265 | 9/1995 | Vidal et al. . |
| 5,462,215 | 10/1995 | Viola et al. ..................... 227/19 |
| 5,470,009 | 11/1995 | Rodak ............................. 227/19 |

APPARATUS FOR APPLYING SURGICAL FASTENERS

BACKGROUND

1. Technical Field

The apparatus relates to surgical fastener applying apparatus, and more particularly to fastener applying apparatus for sequentially firing fasteners having a safety member which prevents reclamping of the apparatus after the fasteners have been fired.

2. Background of Related Art

Surgical devices wherein tissue is first grasped or clamped between opposing jaw structure and then joined by surgical fasteners are well known in the art. In some instruments, a knife is provided to cut the tissue which has been joined by the fasteners. The fasteners are typically in the form of surgical staples, however, two-part polymeric fasteners are also utilized.

Such devices can comprise two elongated members which are used to capture or clamp tissue. Typically, one of the members carries a disposable cartridge which houses a plurality of staples arranged in at least two parallel rows while the other member comprises an anvil which defines a surface for forming the staple legs as the fasteners are driven from the cartridge. The two elongated members are clamped together to capture the tissue between the cartridge and staple forming surface of the anvil. After the two members are clamped, the stapling operation is effected by a pusher which travels longitudinally through the cartridge carrying member, with the pusher acting upon the staples to sequentially eject them from the cartridge. A knife may travel with the pusher between the staple rows to longitudinally cut the stapled tissue between the rows of staples. Such instruments are disclosed in U.S. Pat. Nos. 3,079,606 and 3,490,675.

A later stapler disclosed in U.S. Pat. No. 3,499,591 applies a double row of staples on each side of the incision. This is accomplished by providing a cartridge assembly in which a cam member moves through an elongated guide path between two sets of staggered stapling carrying grooves. Staple drive members are located within the grooves and are positioned in such a manner so as to be contacted by the longitudinally moving cam to effect ejection of the staples. Other examples of such staplers are disclosed in U.S. Pat. No. 4,429,695.

U.S. Pat. No. 4,955,959 to Tomkins, et al discloses a surgical stapler for sequentially firing staples which has a locking mechanism engageable with the cam bar retainer to prevent subsequent movement of the cam bar retainer after the staples have been fired. Thus, the user is prevented from cutting tissue if the cartridge is devoid of staples. Mechanisms for preventing refiring of a spent cartridge are also disclosed in U.S. Pat. No. 4,892,244 to Fox, et al, U.S. Pat. Nos. 5,156,315 and 5,253,793 to Green, et al and U.S. Pat. No. 5,129,570 to Schulze, et al.

WO 92/10976 to Plyley, et al discloses a surgical stapler which has a safety mechanism which prevents the two elongated members, i.e., the anvil carrying section and cartridge carrying section, from being reclamped after the staples have been fired and the elongated members unclamped and separated. A safety member is positioned in the cartridge assembly and is released for movement to a blocking position upon advancement of the cam bars to fire the staples. When the elongated cartridge and anvil carrying sections are separated, the safety member moves to the blocking position to prevent reclamping of the sections. EPO application 545029 to Allen, et al discloses another type of mechanism for preventing reclamping of the cartridge and anvil sections subsequent to the fasteners being fired. In Allen, et al, the knife bar contacts the safety member to move it into the blocking position. As in Plyley, the cartridge and anvil sections need to be separated in order for the safety mechanism to move to the blocking position.

The need exists for an improved safety mechanism which would prevent reclamping of the anvil and cartridge on body tissue after the staples have been fired. This would advantageously inform the user that a new cartridge needs to be reloaded in the apparatus. Furthermore, by preventing reclamping, the user would not actuate the firing knob to advance the knife to cut tissue in the absence of a loaded cartridge. It would be advantageous if such safety mechanism would move to the blocking position without having to fully separate the cartridge and anvil sections.

SUMMARY

A surgical fastener applying apparatus is provided comprising an elongated cartridge half section and an elongated anvil half section relatively movable from an unclamped position to a clamped position to clamp tissue between the cartridge and anvil. A plurality of fasteners are positioned in the cartridge. A firing knob, operatively associated with a pair of cam bars, moves the cam bars longitudinally to sequentially fire the fasteners in a direction transverse to the direction of movement of the cam bars. A safety member is supported in the cartridge section and is movable between a first position to allow relative movement of the cartridge and anvil sections to the clamped position and a blocking position to prevent relative movement of the cartridge and anvil sections to the clamped position after the fasteners have been fired. The cartridge section includes an elongated cartridge supporting member. The safety member pivots away from the longitudinal axis of the cartridge supporting member towards an outer surface thereof. The safety member may be movable from the first position to the blocking position in a direction transverse to the direction of movement of the cam bars and transverse to the direction of movement of the fasteners.

A spring biased clamping lever is pivotally connected to an anvil support member of the anvil section. The safety member, in its initial position, allows movement of the clamping member to a clamped position. In the blocking position, it prevents movement of the clamping lever to the clamped position. Preferably, the safety member is in the form of a spring and the clamping lever has a notch which engages the spring when in the blocking position.

The knife bar preferably retains the safety member in the initial position, whereupon distal movement of the knife bar releases the safety member to allow movement from the initial position to an intermediate position, and unclamping of the clamping lever allows movement of the safety member from the intermediate position to the blocking position.

BRIEF DESCRIPTION OF THE DRAWINGS

Preferred embodiments of the surgical apparatus will be described hereinbelow with reference to the drawings wherein.

DETAILED DESCRIPTION OF THE PREFERRED EMBODIMENTS

Figures 1, 1A:
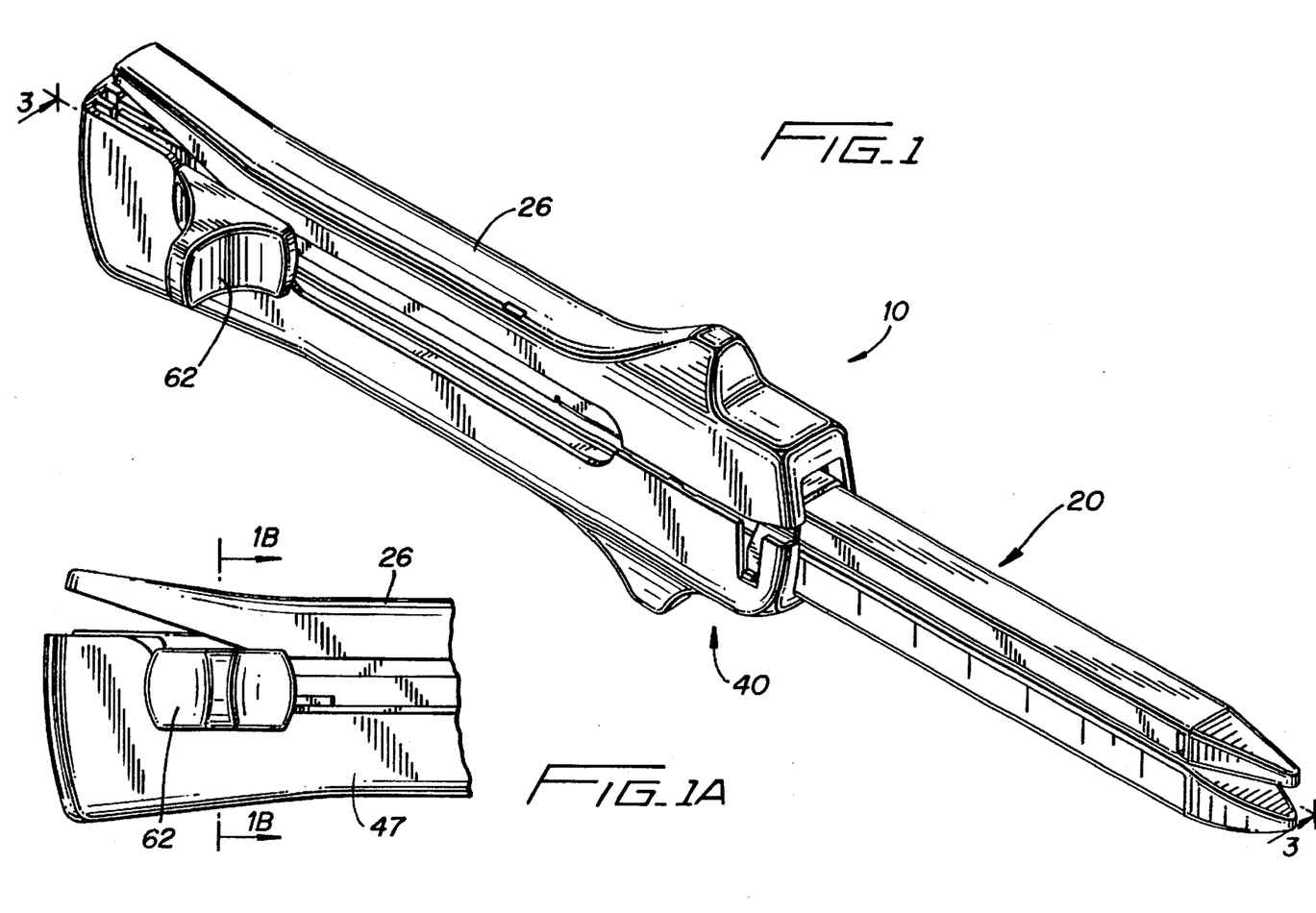
FIG. 1 is a perspective view of the surgical stapling apparatus.
FIG. 1A is a side view of the proximal end of the apparatus of FIG. 1 showing the firing knob in the proximalmost position.
Figure 2:
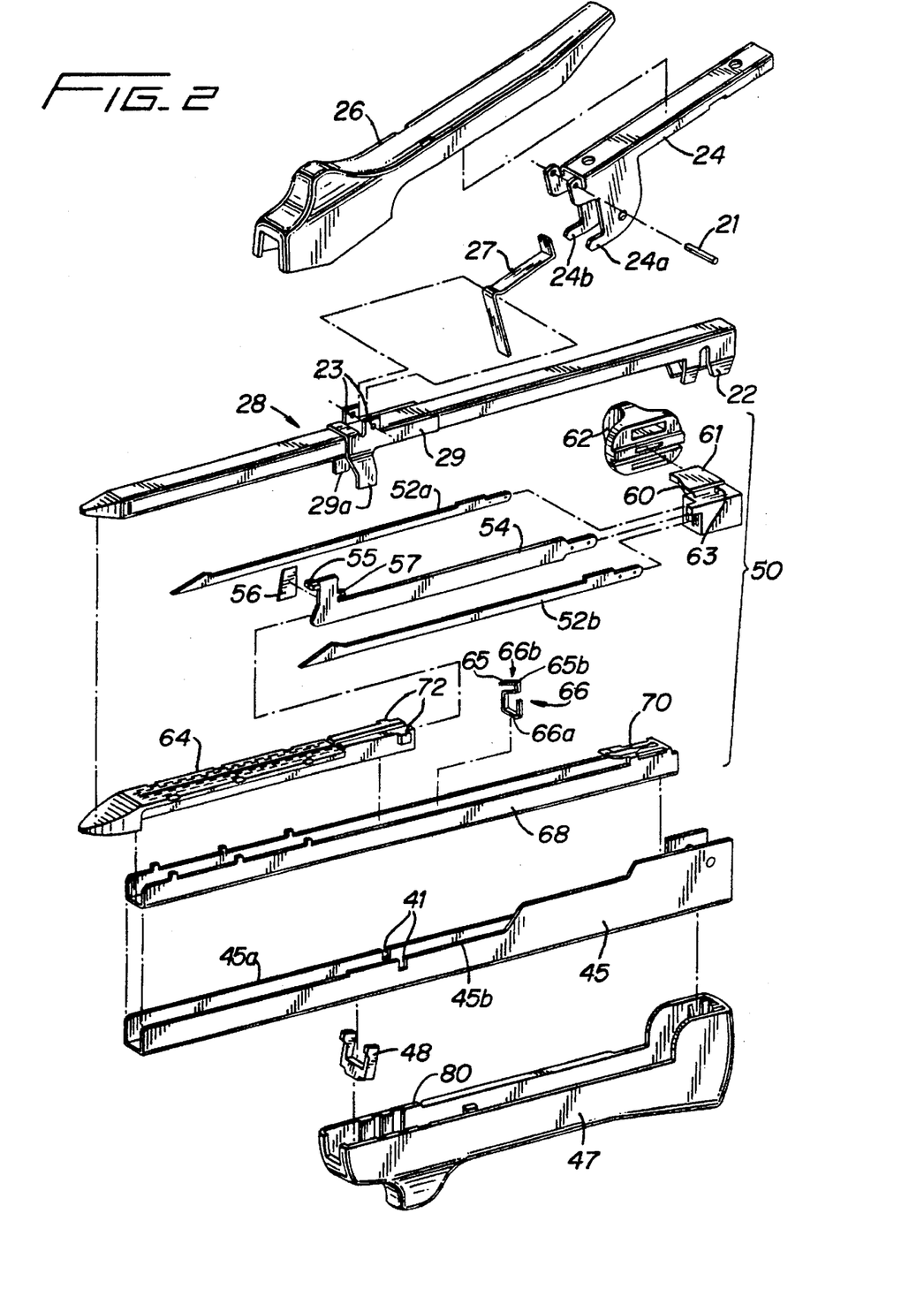
FIG. 2 is an exploded perspective view of the surgical apparatus of FIG. 1.

Referring now to the drawings and more particularly to FIGS. 1 and 2, apparatus 10 includes an elongated anvil half section 20 and an elongated cartridge half section 40. The half sections 20, 40 are adapted to be clamped together in a manner described below to bring cartridge 64 and the opposing anvil surface into close cooperative alignment to clamp tissue therebetween. Cartridge half section 40 includes a plurality of fasteners (not shown) positioned in cartridge 64 which are fired in sequential fashion upon distal movement of firing knob 62. A safety member 66 blocks movement of clamping lever 24 to prevent complete reclamping of the cartridge and anvil half sections 20, 40, respectively, after the fasteners have been fired. The structure and operation of the safety member 66 will be described in more detail below.

Figure 1B:
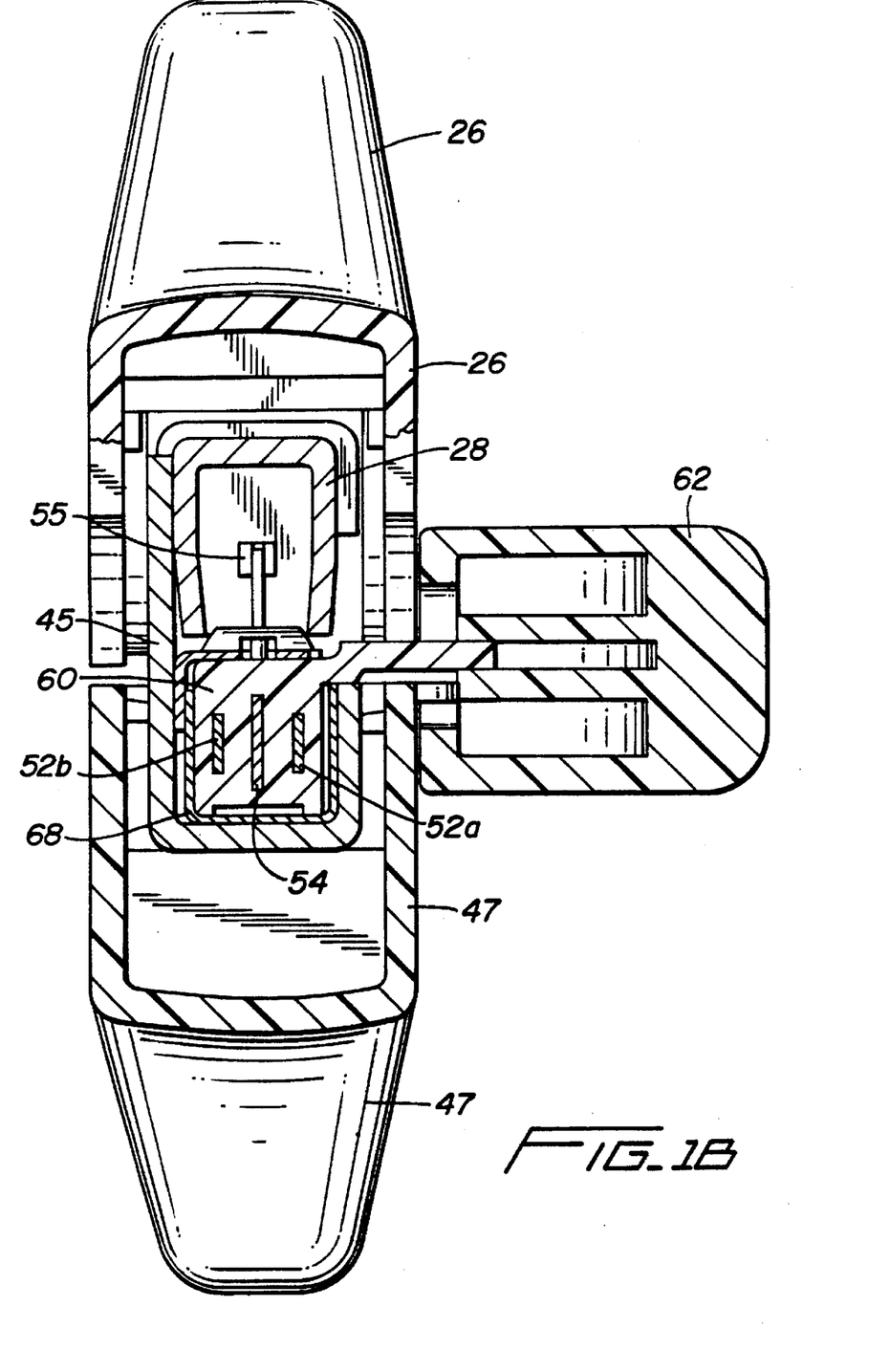
FIG. 1B is a cross-sectional view taken along lines 1B—1B of FIG. 1A.

Turning now to FIGS. 1B and 2, anvil half section (or anvil supporting section) 20 includes an elongated anvil channel 28, clamping lever 24, and a clamping lever housing 26. A plurality of depressions (not shown) for forming the fasteners ejected from cartridge 64 are formed in the anvil surface of anvil channel 28 for positioning opposite the cartridge 64. The depressions are arranged in rows corresponding to the double pair of parallel rows of fasteners in cartridge 64. Clamping lever 24 is seated within clamping lever housing 26 and is pivotally connected to anvil channel 28 via transverse pin 21 extending through openings 23 in tissue stop 29. Lever spring 27 biases clamping lever 24 to the open (unclamped) position. Clamping fingers 24a, 24b of clamping lever 24 are adapted to be positioned under channel clamp 48 and function to bring the cartridge and anvil half sections together in a manner described below.

Cartridge half section (or cartridge supporting section) 40 includes a cartridge housing 47, an elongated cartridge support or channel 45 mounted therein, and a disposable loading unit designated generally by reference numeral 50. Cartridge channel 45 includes parallel upstanding outer walls 45a, 45b within which disposable loading unit 50 is removably mounted.

Disposable loading unit 50 includes a cartridge support 68, cartridge 64 housing the fasteners, elongated cam bars 52A, 52B, knife bar 54, cam bar retainer 60, and firing knob 62. Tabs 72 of cartridge 64 are seated within slots 41 of cartridge channel 45 when the disposable loading unit is loaded in the apparatus. Cam bars 52A, and 52B, and knife bar 54 are mounted at their proximal ends to cam bar retainer 60 which is mounted to firing knob 62 via flange 61. Knife blade 56 is mounted to the distal end of knife bar 57 and has a sharpened edge to cut tissue between the two pairs of parallel rows of fasteners when knife bar 57 is advanced distally. Shoes 55 are positioned at the distal end of knife bar 54 and travel within a slot in anvil channel 28. These shoes as well as the operation of the firing knob and cam bars to fire the fasteners are disclosed in U.S. Pat. No. 4,520,817, the contents of which are incorporated herein by reference. In brief, advancement of the firing knob 62 distally, slides the cam bars 52a, 52b and knife bar 54 distally, with the knife slightly trailing the cam bars. Each cam bar sequentially engages a pair of staple drivers (not shown) positioned in cartridge 64 to sequentially drive the staples through the openings in cartridge 64 in a transverse direction towards the anvil surface of anvil channel 28. The knife bar 54, positioned between the cam bars 52a, 52b as shown in FIG. 1B, cuts tissue between the staple rows.

It should be noted that cartridge 64 can hold either metal staples or polymeric staples such as two-part fasteners of the type disclosed, for example, in U.S. Pat. No. 5,156,614, the contents of which are incorporated herein by reference.

Shipping interlock 70, which is designed to prevent premature firing of the fasteners during shipping and handling, contains a slotted portion of varying width to receive projection 63 of cam bar retainer 60. When firing knob 62 is slid distally with sufficient force, projection 63 enters the widened slot portion of shipping interlock 60 and movement of firing knob 62 is unimpeded.

Figure 4:
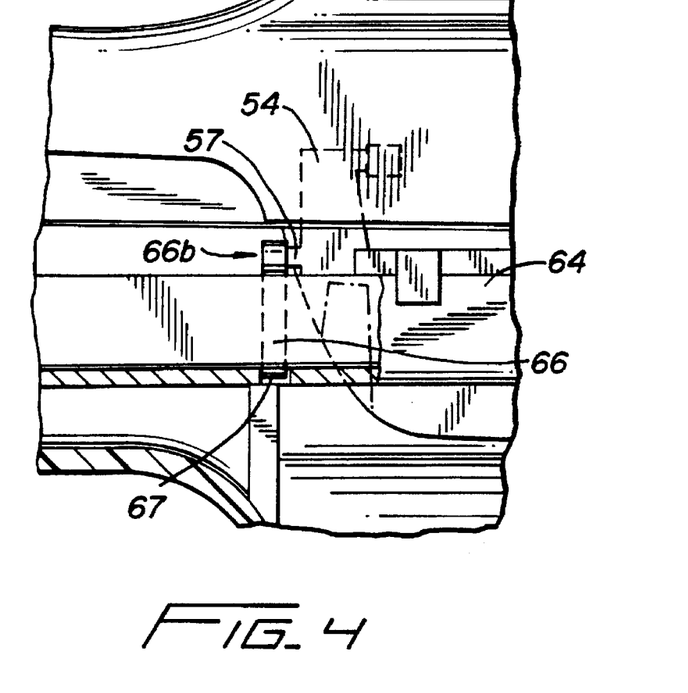
FIG. 4 is an enlarged side view in partial cross section illustrating the safety member in the initial position prior to firing of the fasteners.
Figure 4A:
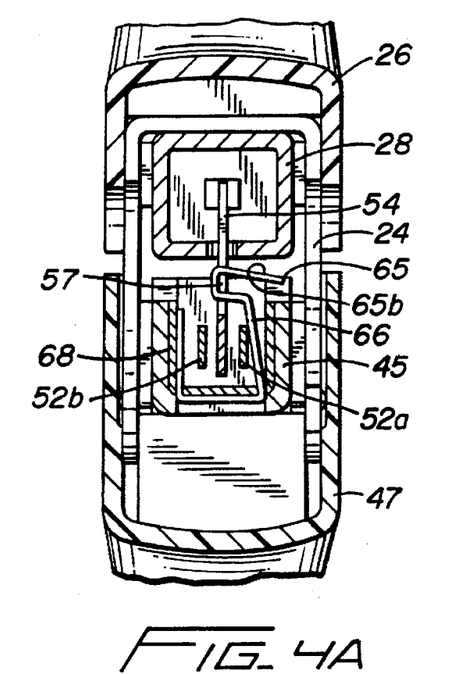
FIG. 4A is a cross-sectional view taken along lines 4A—4A of FIG. 3 and corresponding to the position of the safety member in FIG. 4.

Cantilevered safety spring 66 wraps around the cartridge support 68 and is positioned in a slot in the floor of cartridge channel 45 (see also FIG. 4A). Safety spring 66 has a U-shaped mounting portion 66a which is secured around cartridge support 68 and a U-shaped blocking portion 66b having a distal tip 65 and an upper surface 65b. Safety spring 66 is biased outwardly away from the longitudinal axis of cartridge channel 68 towards wall 80 of cartridge housing 47. The function of safety spring 66 is discussed in more detail below.

Figure 3:
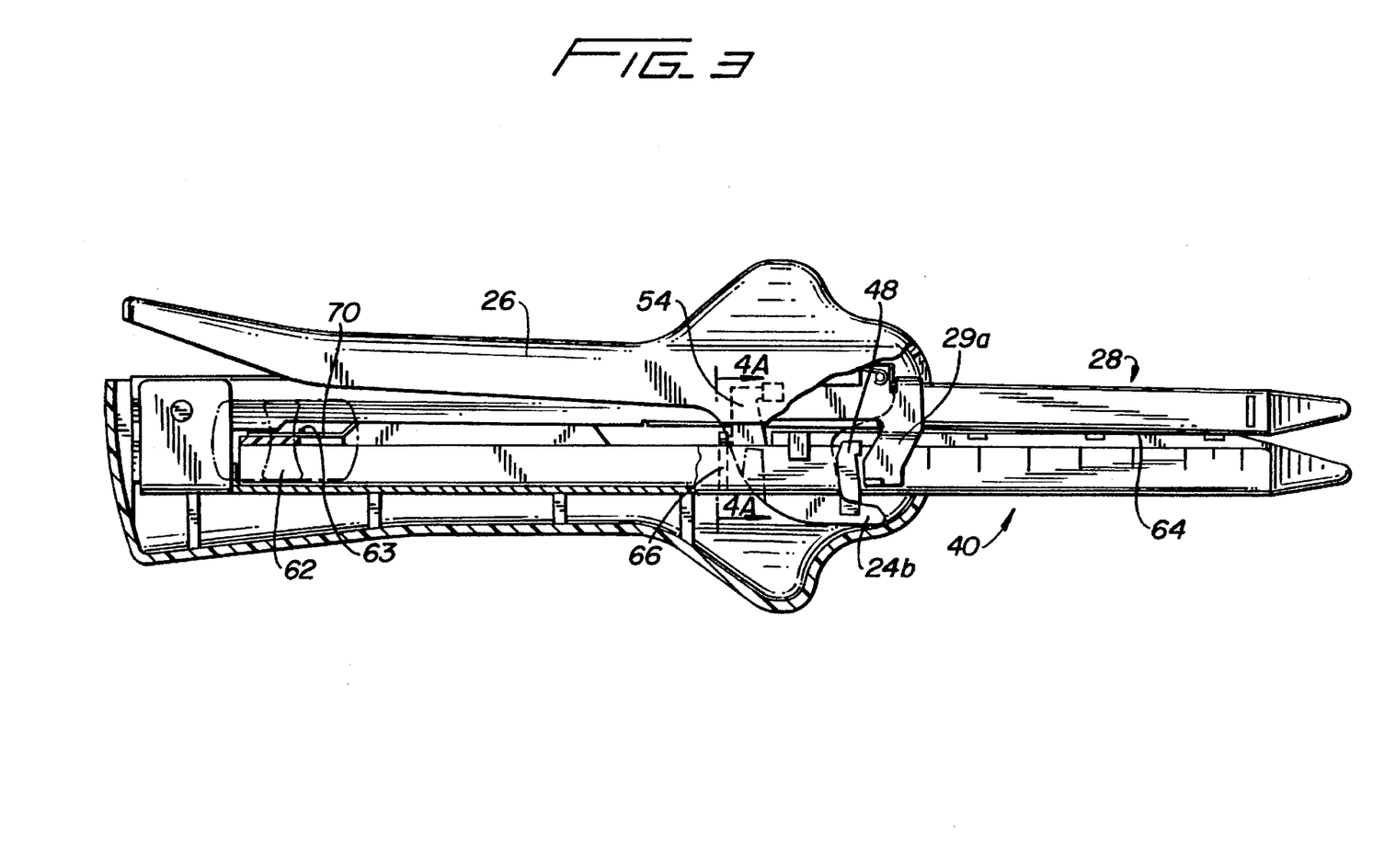
FIG. 3 is a side view in partial cross section showing the apparatus prior to firing of the fasteners and the safety member retained in the initial (non-blocking) position.

With reference to FIGS. 2 and 3, channel clamp 48 is mounted in cartridge channel 45. Fingers 24a, 24b of the clamping lever 24 extend underneath channel clamp 48 to retain the cartridge and anvil half sections 40, 20 in a clamped position. Fingers 29a of tissue stop 29 straddle cartridge channel 45 to help restrict lateral movement of the cartridge and anvil half sections. Thus, to clamp the anvil and cartridge half sections 20, 40, together to retain tissue between cartridge 64 and the anvil surface, proximal clamping fingers 22 of anvil channel 28 are inserted over a proximally positioned transverse pin (not shown) in cartridge channel 45. Tissue stop fingers 29a straddle cartridge channel 45, and clamp lever fingers 24a, 24b are positioned underneath cartridge clamp 48. The clamping lever 24 is then pivoted downwardly towards anvil channel 28, thereby forcing the anvil surface and cartridge 64 into close cooperative alignment. This movement of clamping lever 24 to the clamped position fully clamps the cartridge and anvil half sections 40, 20 and secures the half sections in their clamped position since the cooperation of cartridge clamp 48 and lever fingers 24a, 24b in the clamped position of the clamping lever 24 prevent separation of the cartridge half sections.

Figure 3A:
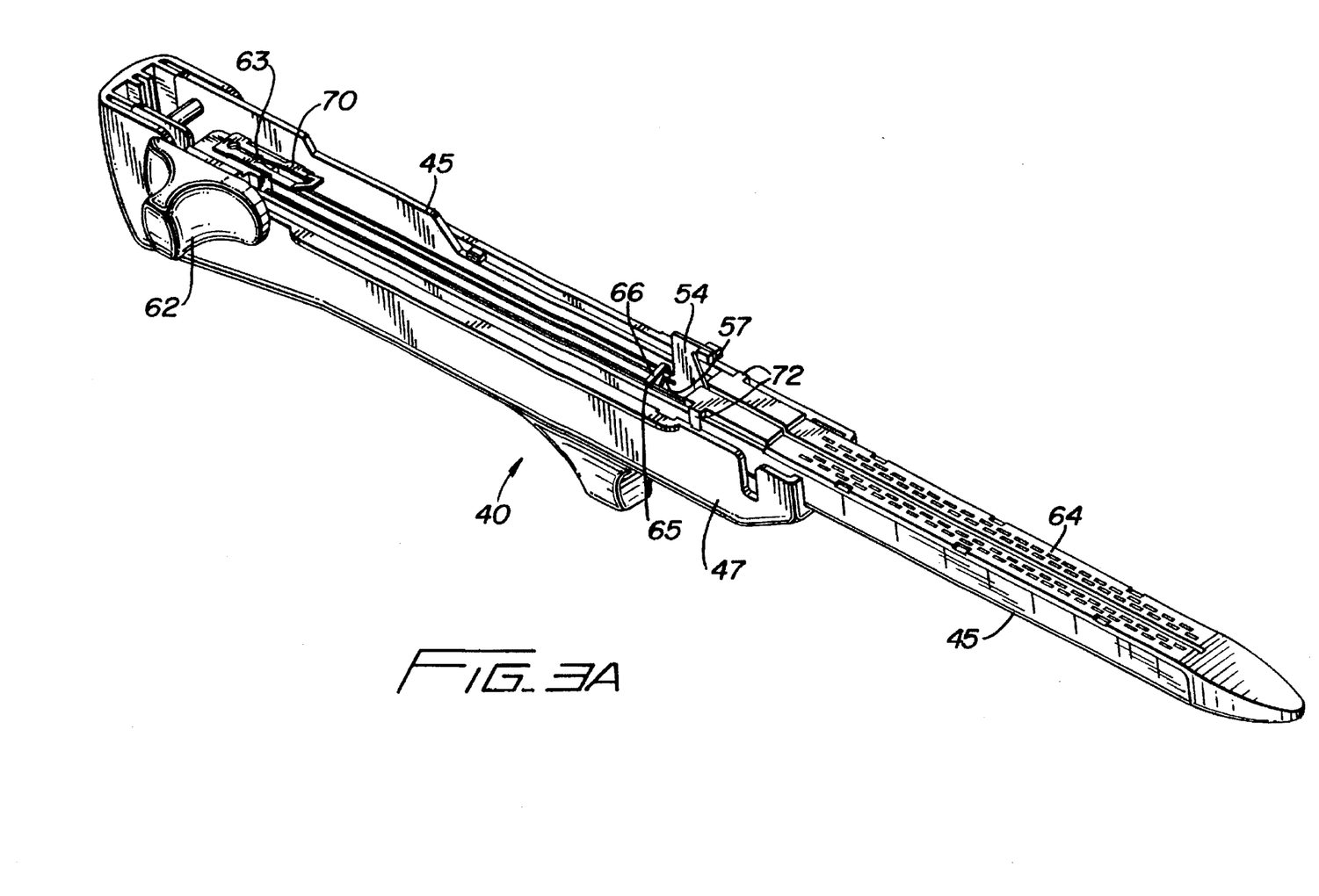
FIG. 3A is a perspective view of the cartridge half section of the apparatus of FIG. 1 showing the safety member retained in the initial position prior to firing of the fasteners.

Turning now to the safety member 66, as briefly noted above, safety member 66 prevents complete reclamping of the apparatus 10 after the staples have been fired from cartridge 64 and the clamping lever 24 is pivoted to the unclamped position to allow separation of cartridge and anvil half sections 20, 40. More specifically, with reference first to FIG. 3, the apparatus 10 is shown in the fully clamped and pre-fired position. That is, clamping lever 24 is in the clamped position (adjacent the upper surface of anvil channel 28) and firing knob 62 is in the proximalmost position with projection 63 of cam bar retainer 60 engaging the shipping interlock 70 to maintain the cam bar retainer 60 in the initial position. With reference to FIGS. 3A, 4 and 4A, in this pre-fired position, safety member 66 is retained in the non-blocking position by projection 57 of knife bar 54. In this non-blocking position, distal tip 65 is biased inwardly out of alignment with clamping lever 24 and consequently safety spring 66 does not block movement of clamping lever 24. Thus, the cartridge and anvil half sections 20 and 40 can be unclamped and reclamped on the body tissue if desired.

Figure 5:
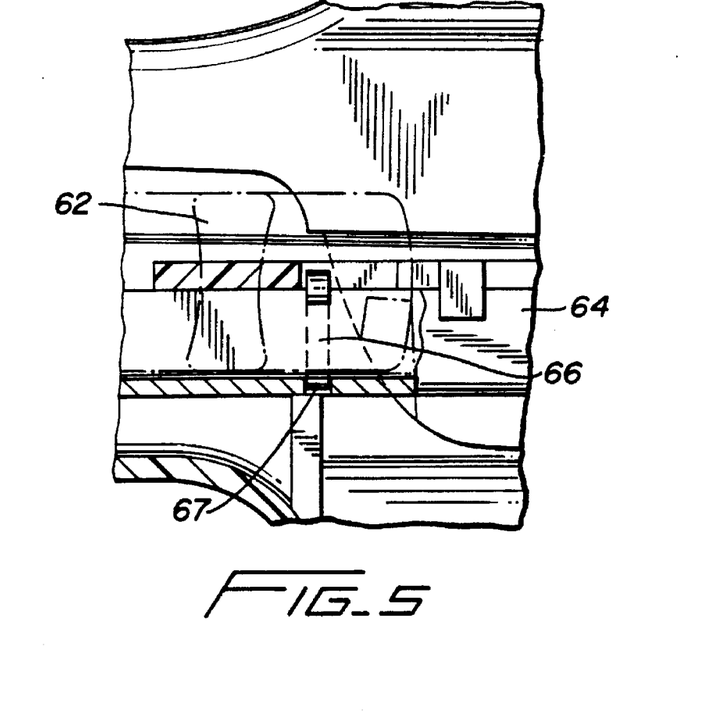
FIG. 5 is an enlarged side view in partial cross section illustrating the safety member in an intermediate position subsequent to firing of the fasteners but prior to separation of the cartridge and anvil half sections.
Figure 5A:
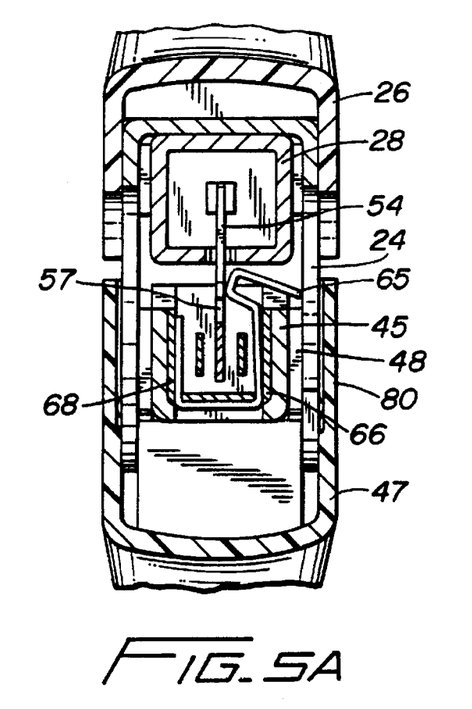
FIG. 5A is a cross-sectional view similar to FIG. 4A except showing the safety member in the intermediate position corresponding to the position of the safety member shown in FIG. 5.

Once the tissue is properly clamped between the cartridge 64 and the anvil clamping lever 24 is in the clamped position bringing the cartridge and anvil surface into close cooperative alignment and retaining the half sections 20, 40 together, firing knob 62 is slid longitudinally, overcoming the shipping interlock 70 as projection 63 enters the widened slot portion as described above. This advances the cam bars 52A, 52B and knife bar 54 through cartridge 64 to sequentially apply the four parallel rows of staples and simultaneously cut the tissue between the double pair of rows. As knife bar 54 is advanced distally, safety spring 66 is released from projection 57 of knife bar 54 (FIG. 5) and pivots outwardly away from the longitudinal axis towards the outer side edge 80 of cartridge housing 47 as shown in FIG. 5A. In this intermediate position, safety spring 66 is prevented from further pivotal movement by the abutment of distal tip 65 with clamping lever 24.

Figure 6A:
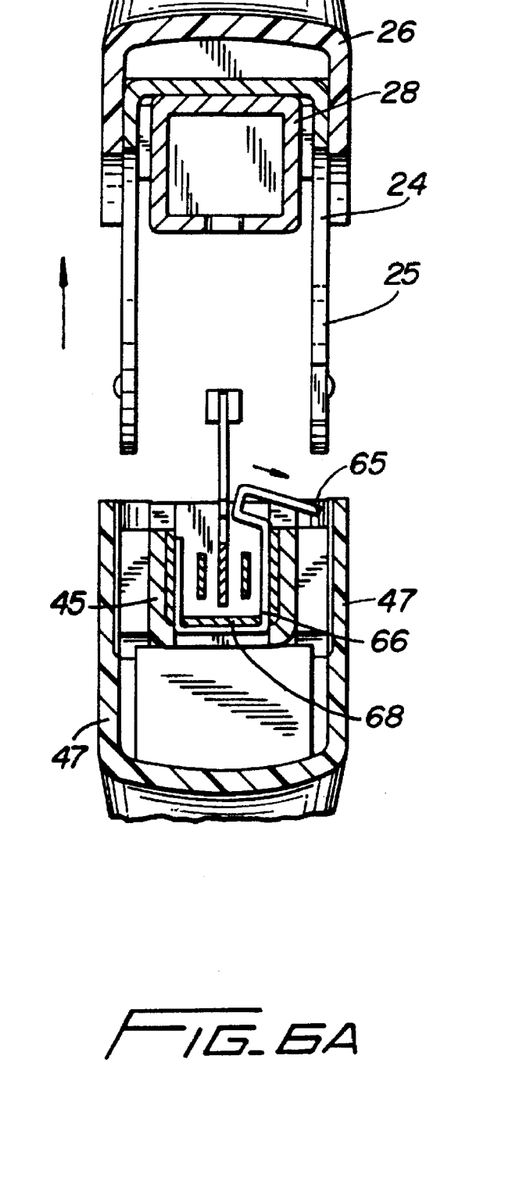
FIG. 6A is a cross-sectional view similar to FIG. 4A except showing separation of the anvil and cartridge half sections and the safety member in the blocking position.
Figure 6B:
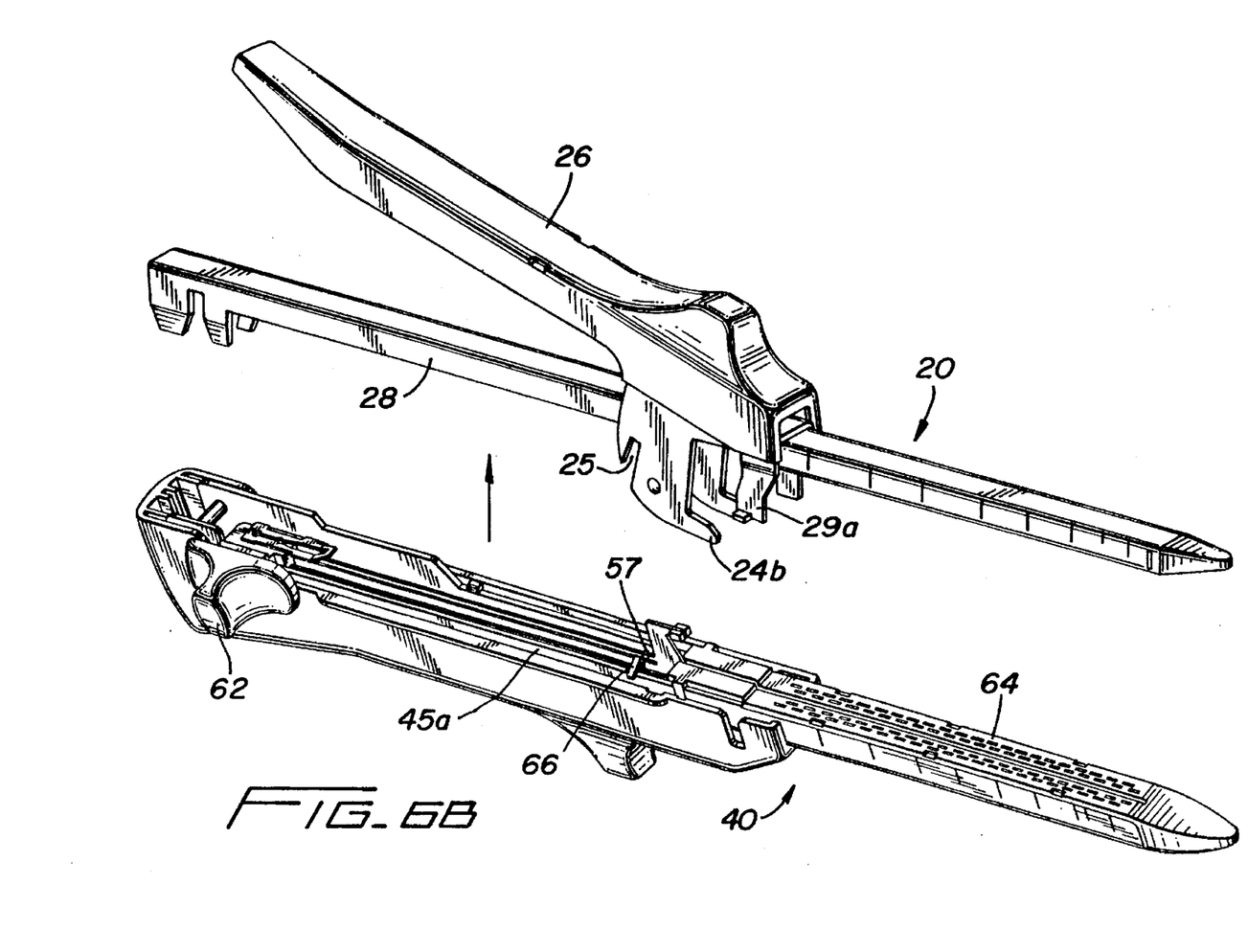
FIG. 6B is a perspective view showing the cartridge and anvil half sections separated and the safety member in the blocking position.
Figure 6C:
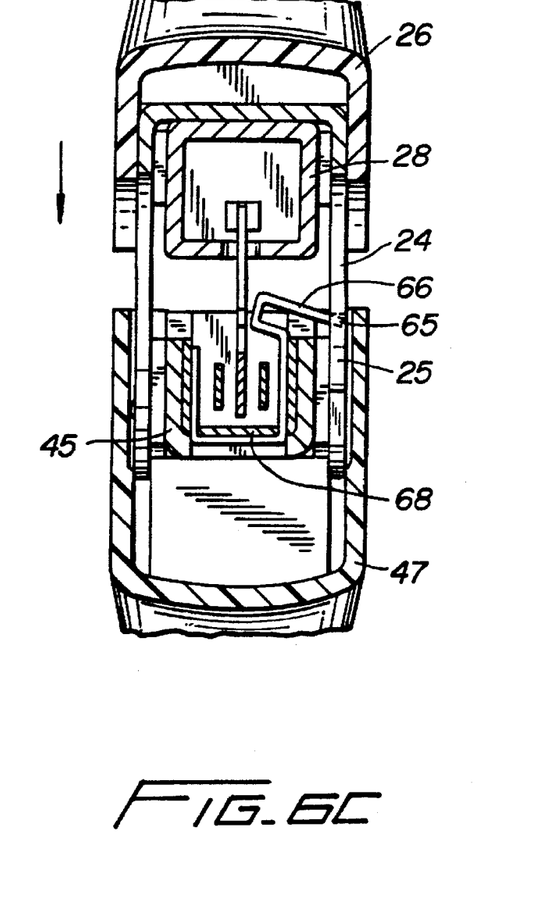
FIG. 6C is a cross-sectional view similar to FIG. 4A except showing the safety member in the blocking position and in contact with the clamping lever to prevent reclamping of the cartridge and anvil half sections.
Figures 6D, 6E:
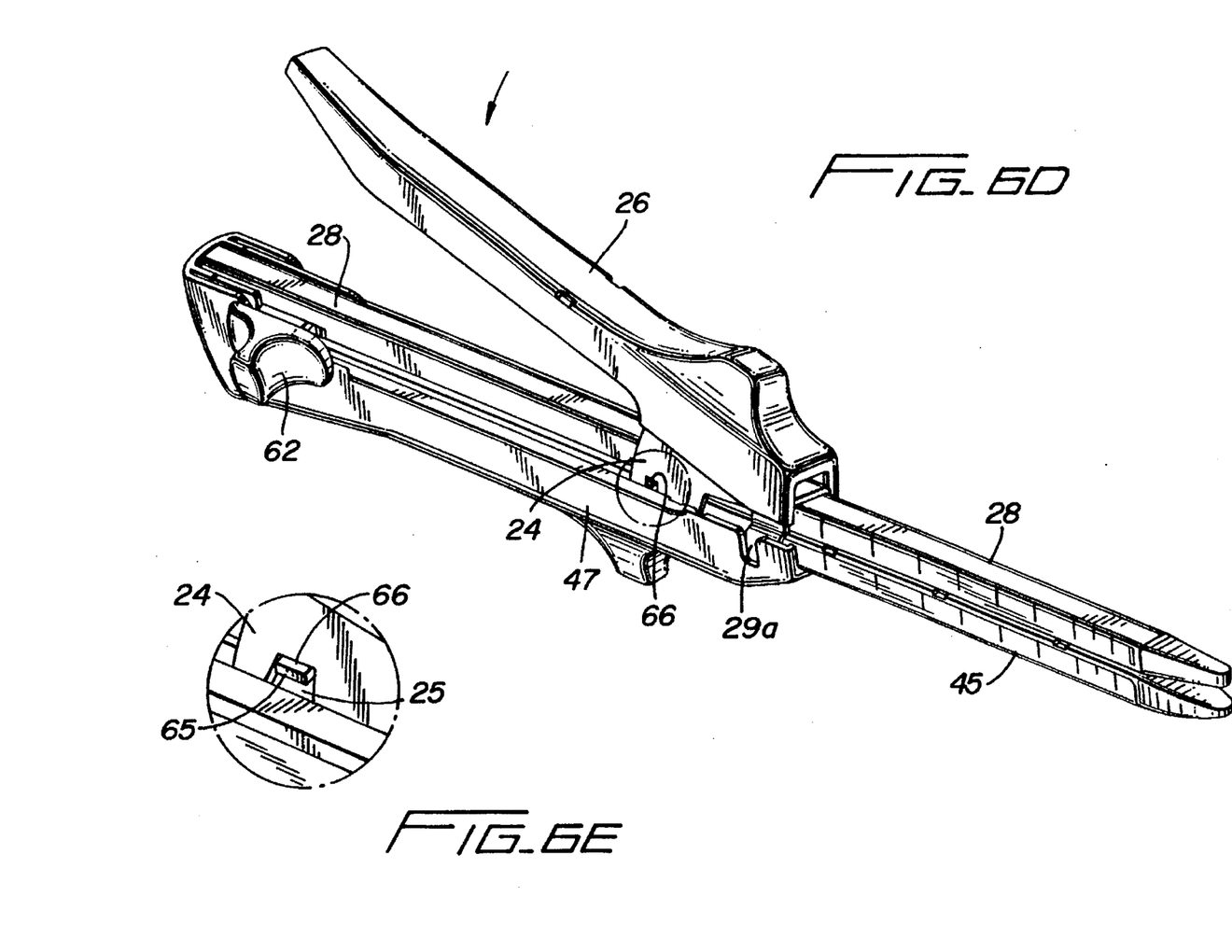
FIG. 6D is a perspective view showing the safety member in the blocking position to prevent movement of the clamping lever to its clamped position.
FIG. 6E is an enlarged view showing the safety member in the blocking position and in engagement with the clamping lever.

When clamping lever 24 is pivoted away from anvil channel 28 to allow release of fingers 24a, 24b from cartridge clamp 48 to enable the anvil and cartridge half sections 20, 40 to be separated, spring 66 is allowed to pivot in the direction of the arrow of FIG. 6A to the blocking position. This blocking position of safety spring 66 is also shown in FIG. 6B where the distal tip 65 extends beyond the outer wall 45a of channel member 45. In this blocking position, if the user attempts to reclamp anvil and cartridge half sections 20 and 40, although the fingers 24a, 24b of clamping lever 24 can be slid under cartridge clamp 48, clamping lever 24 cannot be closed since upon movement towards anvil channel 28, notch 25 of clamping finger 24b engages the upper surface 66 of distal tip 65 of safety spring 66 (see FIGS. 6C–6E). Thus, safety spring 66 prevents pivotal movement of clamping lever 24 to the clamped position and the cartridge and anvil half sections 40, 20 cannot be fully clamped to effectively clamp tissue between cartridge 64 and the anvil surface. This alerts the user that the fasteners of cartridge 64 have been fired. The user can then remove the spent cartridge (with disposable loading unit 50) and replace it with a fresh disposable loading unit containing a loaded cartridge. This fresh disposable loading unit will have the spring 66 retained in the non-blocking position by the projection 57 of the knife bar 54, thereby allowing the cartridge and anvil half sections 40, 20 to be fully clamped.

It is apparent that the safety spring 66 prevents full pivotal movement of clamping lever 24, thereby preventing relative movement of the cartridge and anvil half sections to the fully clamped position after the fasteners have been fired. When these half sections cannot be fully moved relative to each other to properly clamp tissue between the cartridge 64 and anvil surface, the user is alerted to the fact that a new disposable loading unit must be inserted. Also, unnecessary clamping on tissue is prevented.

It will be understood that various modifications may be made to the embodiments disclosed herein. For example as an alternative to the cantilevered safety spring, a spring loaded pin movable in an axial direction could be provided to interfere with the clamping lever. Also, different notch, indentation or detent configurations could be provided in the clamping lever to cooperate with the safety member. Therefore, the above description should not be construed as limiting but merely as exemplifications of preferred embodiments. Those skilled in the art will envision other modifications within the scope and spirit of the claims appended hereto.

What is claimed is:

1. A surgical fastener applying apparatus comprising:
 an elongated cartridge section;
 an elongated anvil section, the cartridge and anvil sections being relatively movable from an unclamped position to a fully clamped position to clamp tissue therebetween, the anvil section including a pivotable clamping lever, wherein movement of the clamping lever from a first position to a second position moves the cartridge and anvil sections to the fully clamped position;
 a plurality of cam bars supported in the cartridge section;
 a plurality of fasteners supported in the cartridge section;
 a firing knob operatively associated with the cam bars to move the cam bars longitudinally to sequentially fire the plurality of fasteners in a direction transverse to the direction of movement of the cam bars; and
 a safety member supported in the cartridge section, the safety member interacting with the clamping lever and mounted for movement between an initial position to allow movement of the clamping lever to the second position and a blocking position to block movement of the clamping lever to the second position after the fasteners have been fired to thereby prevent relative movement of the cartridge and anvil sections to the fully clamped position.

2. A surgical fastener applying apparatus according to claim 1, wherein the clamping lever has a notch which engages the safety member in the blocking position.

3. A surgical fastener applying apparatus according to claim 2, wherein the notch engages an upper surface of the safety member.

4. A surgical fastener applying apparatus according to claim 2, wherein the safety member comprises a cantilevered spring biased toward the blocking position.

5. A surgical fastener applying apparatus according to claim 4, further comprising a knife bar supported in the cartridge section, the knife bar retaining the spring in the initial position.

6. A surgical fastener applying apparatus according to claim 5, wherein movement of the knife bar distally upon distal advancement of the firing knob releases the spring to allow it to move towards the blocking position.

7. A surgical fastener applying apparatus according to claim 1, wherein the safety member comprises a spring, the spring being movable to an intermediate position prior to movement to the blocking position.

8. A surgical fastener applying apparatus according to claim 7, wherein movement of the clamping lever to the first position after the fasteners have been fired allows movement of the safety member from the intermediate position to the blocking position.

9. A surgical fastener applying apparatus comprising:
  an elongated cartridge section having an elongated cartridge supporting member, the cartridge supporting member having a longitudinal axis and first and second substantially parallel outer walls;
  an elongated anvil section, the cartridge and anvil sections being relatively movable from an unclamped position to a clamped position to clamp tissue therebetween;
  a plurality of cam bars supported in the cartridge supporting member;
  a plurality of fasteners supported in the cartridge supporting member;
  a firing knob operatively associated with the cam bars to move the cam bars longitudinally to sequentially fire the plurality of fasteners in a direction transverse to the direction of movement of the cam bars; and
  a blocking member supported in the cartridge supporting member and mounted for movement between a non-blocking position to allow relative movement of the cartridge and anvil sections to the clamped position and a blocking position to prevent relative movement of the cartridge and anvil sections to the clamped position after the fasteners have been fired, the blocking member pivoting toward the blocking position in a direction away from the longitudinal axis of the cartridge supporting member and toward the first outer wall of the cartridge supporting member.

10. A surgical fastener applying apparatus according to claim 9, further comprising a knife bar supported in the cartridge supporting member, the knife bar retaining the blocking member in the non-blocking position.

11. A surgical fastener applying apparatus according to claim 10, wherein the safety member is spring biased toward the blocking position.

12. A surgical fastener applying apparatus according to claim 11, wherein the knife bar has a projecting surface to retain the safety member in the non-blocking position.

13. A surgical fastener applying apparatus according to claim 12, wherein movement of the knife bar distally releases the safety member to allow movement towards the blocking position.

14. A surgical fastener applying apparatus according to claim 9, wherein the safety member comprises a cantilevered spring biased toward the blocking position.

15. A surgical fastener applying apparatus according to claim 14, wherein the anvil section includes a pivotably mounted clamping lever, wherein the spring abuts the clamping lever in the blocking position to prevent movement of the clamping lever.

16. A surgical fastener applying apparatus according to claim 15, wherein the clamping lever includes a notch configured to engage a portion of the spring in the blocking position.

17. A surgical fastener applying apparatus according to claim 16, wherein movement of the clamping lever from a clamping position to an unclamping position after the fasteners have been fired allows movement of the spring from the intermediate position to the blocking position.

18. A surgical fastener applying apparatus according to claim 14, wherein the spring is movable to an intermediate position prior to movement to the blocking position.

19. A surgical fastener applying apparatus according to claim 18, wherein movement of the clamping lever from a clamping position to an unclamping position after the fasteners have been fired allows movement of the spring from the intermediate position to the blocking position.

* * * * *